United States Patent [19]

Smith et al.

[11] 4,158,676
[45] Jun. 19, 1979

[54] ISOMERIZATION PROCESS

[75] Inventors: Fritz A. Smith, Haddonfield, N.J.; Lloyd L. Breckenridge; Albert B. Schwartz, both of Philadelphia, Pa.

[73] Assignee: Mobil Oil Corporation, New York, N.Y.

[21] Appl. No.: 915,414

[22] Filed: Jun. 14, 1978

Related U.S. Application Data

[63] Continuation-in-part of Ser. No. 813,911, Jul. 8, 1977, abandoned.

[51] Int. Cl.² .............................................. E07C 15/02
[52] U.S. Cl. .................................................... 585/481
[58] Field of Search ........................ 260/668 A, 668 R

[56] References Cited

U.S. PATENT DOCUMENTS

| | | | |
|---|---|---|---|
| 3,293,314 | 12/1966 | Brodbeck | 260/668 A |
| 3,644,200 | 2/1972 | Young | 360/668 A |
| 3,856,872 | 12/1974 | Morrison | 260/668 A |
| 3,856,873 | 12/1974 | Burress | 260/668 A |
| 3,992,466 | 11/1976 | Plank et al. | 260/668 A |

*Primary Examiner*—Veronica O'Keefe
*Attorney, Agent, or Firm*—C. A. Huggett; R. W. Barclay; C. J. Speciale

[57] ABSTRACT

An improved process is provided for catalytic isomerization of monocyclic methyl-substituted aromatic hydrocarbon compounds of from 8 to 10 carbon atoms contained in a feedstock also containing ethylbenzene in a reaction zone maintained under conditions such that said isomerization is accomplished in the vapor phase. The catalyst for the process contains zeolite characterized by a constraint index, hereinafter defined, within the approximate range of 1 to 12. The improvement in the process comprises contacting the catalyst, in situ, with one or more basic nitrogen compounds or precursors thereof.

32 Claims, 1 Drawing Figure

ISOMERIZATION PROCESS

CROSS-REFERENCE TO RELATED CASE

This is a continuation-in-part of application Ser. No. 813,911, filed July 8, 1977, now abandoned.

BACKGROUND OF THE INVENTION

1. Field of the Invention

The present invention relates to a new and useful improvement in a process for the isomerization of monocyclic methyl-substituted aromatic hydrocarbon feedstock. The process comprises the use of a specific catalyst in a vapor phase reaction, said catalyst containing a crystalline aluminosilicate zeolite characterized by a constraint index, hereinafter defined, within the approximate range of 1 to 12.

2. Description of the Prior Art

The catalytic rearrangement of alkyl groups present in alkyl aromatic hydrocarbons to provide one or more products suitable for use in the petroleum and chemical industries has heretofore been effected by a wide variety of catalysts. Acidic halides such as aluminum chloride, aluminum bromide, boron trifluoride—hydrogen fluoride mixtures, etc. have been used in the rearrangement of alkyl benzenes to provide valuable intermediates which find utility in the synthesis of rubber, plastic, fibers and dyes. Other catalysts which have been used include solid siliceous cracking-type catalysts such as silica-alumina and clays and platinum deposited on silica-alumina. Although various catalysts possess one or more desired characteristics, a majority of catalysts heretofore employed suffer from several disadvantages. Acidic halides such as aluminum chloride, for example, are partially soluble in the feed material and are easily lost from the catalyst zone. Catalysts of this type are also uneconomical because of their extreme corrosiveness and requirements for recovery from the effluent products. Other catalysts of the heterogeneous type, such as silica-alumina, platinum on alumina, etc., do not possess sufficient acidity to provide effective conversion and necessitate the use of relatively high temperatures above the order of 800° F. to 950° F. High temperatures frequently lead to coke formation which lowers the yield of desired product and necessitates frequent regeneration of the catalyst to remove coke. This results in reducing on-stream time and leads to high catalyst consumption due to loss of catalyst activity. Heterogeneous catalyst such as the crystalline aluminosilicates, both natural and synthetic, possess sufficient acidity but suffer the disadvantage of poor selectivity and aging as evidenced by "coke" make and the excessive amounts of disproportionated product formed in isomerization reactions.

A process in the art for isomerization of xylene is Octafining, extensively discussed in the literature as exemplified by:

1. Pitts, P. M., Connor, J. E., Leun, L. N., Ind. Eng. Chem., 47, 770 (1955).
2. Fowle, M. J., Bent, R. D., Milner, B. E., presented at the Fourth World Petroleum Congress, Rome, Italy, June 1955.
3. Ciapetta, F. G., U.S. Pat. No. 2,550,531.
4. Ciapetta, F. G., and Buck, W. H., U.S. Pat. No. 2,589,189.
5. Octafining Process, Process Issue, Petroleum Refinery, 1st Vol. 38 (1959), No. 11, Nov., p. 278.

The catalyst for use in such process is platinum on silica-alumina.

An improved catalyst for use in Octafining plants is taught by U.S. Pat. No. 3,856,872 to be of the ZSM-5 type of zeolite, whereby the process operates at high space velocities. Further, a process utilizing ZSM-5 type zeolites in acid form for vapor-phase conversion of a feedstock containing mixed $C_8$ aromatics in the absence of added hydrogen is taught by U.S. Pat. No. 3,856,873. Even in such processes, especially when the catalyst has increased acid activity, there is a loss of xylene, the primary isomerization product, presumably due in part to disproportionation of xylenes and/or transalkylation of xylenes with any ethylbenzene which may be present in the reaction system.

It is hereby proposed and demonstrated that by in situ contacting such a catalyst with a basic nitrogen compound or precursor thereof, loss of primary isomerization product is substantially reduced.

The use of nitrogen compounds for various reasons in hydrocracking and reforming in the presence of catalyst other than that for use herein is known in the art. Examples of such art include U.S. Pat. Nos. 2,849,377 (reforming); 3,657,110 (hydrocracking) and 3,694,345 (hydrocracking). Isomerization of alkyl aromatic compounds in the presence of nitrogen compounds to equilibrium products over catalyst other than that for use herein is taught in U.S. Pat. Nos. 3,293,314 and 3,644,200. The catalyst for use in the process of U.S. Pat. No. 3,293,314 is a solid acidic mixed metal-oxide catalyst, e.g., a silica-alumina mixture, having equilibration (tending to produce equilibrium products) and coke forming activities. Unfortunately, such catalyst materials lose their ability to maintain their equilibration tendency and, therefore, there is a decrease in desirable isomeric products as the catalysts age.

SUMMARY OF THE INVENTION

This invention relates to a new and useful improvement in vapor phase isomerization of monocyclic methyl-substituted aromatic hydrocarbons of from 8 to 10 carbon atoms contained in a feedstock which also contains ethylbenzene. The isomerization reaction is carried out in the presence of a catalyst composition containing a crystalline aluminosilicate zeolite characterized by a constraint index of from about 1 to about 12. The zeolite of the catalyst composition may or may not contain, as replacement for at least a part of the original alkali metal cations, cations of a metal of Group VIII of the Periodic Table of Elements, e.g., nickel, platinum, iron and/or cobalt. Further, the zeolite of the catalyst composition may contain, as replacement for at least a part of the original alkali metal cations, hydrogen or hydrogen precursor cations. The improvement resides in contacting the catalyst, in situ, with one or more basic nitrogen compounds or precursors thereof such that the ratio of nitrogen atoms/aluminum atom in the zeolite component of the catalyst equals from about 0.01 to about 1.0, preferably from about 0.1 to about 1.0, whereby loss of primary isomerization product is minimized.

BRIEF DESCRIPTION OF THE DRAWING

The FIGURE drawing depicts data generated in examples hereinafter presented by a plot of xylene loss in mole percent v. ethylbenzene conversion in mole percent for both untreated catalyst and treated catalyst.

DESCRIPTION OF SPECIFIC EMBODIMENTS

The catalyst composition useful in this invention contains a crystalline aluminosilicate zeolite characterized by a constraint index of from 1 to about 12, non-limiting examples of which include ZSM-5, ZSM-11, ZSM-12, ZSM-35, and ZSM-38. Preferred zeolites for use in the present invention are those with a SiO$_2$/Al$_2$O$_3$ mole ratio of least about 12.

Zeolite ZSM-5 is taught by U.S. Pat. No. 3,702,886, issued Nov. 14, 1972, the disclosure of which is incorporated herein by reference. In a preferred synthesized form, the zeolite ZSM-5 for use in the catalyst composition useful in this invention has a formula, in terms of mole ratios of oxides in anhydrous state, as follows:

$$(0.9.\pm 0.2)M_2O/n:Al_2O_3:xSiO_2$$

wherein M is selected from the group consisting of a mixture of alkali metal cations, especially sodium, and tetraalkylammonium cations, the alkyl groups of which preferably contain 2 to 5 carbon atoms, and x is at least 5. Particularly preferred is a zeolite having the formula in the anhydrous state as follows:

$$(0.9\pm 0.2)M_2O/n:Al_2O_3:ZSiO_2$$

wherein Z is from greater than 30 to about 350 or higher.

Zeolite ZSM-11 is taught by U.S. Pat. No. 3,709,979, issued Jan. 9, 1973, the disclosure of which is incorporated herein by reference. In the as synthesized form, the zeolite ZSM-11 for use in the catalyst composition useful in this invention has a formula, in terms of mole ratios of oxides in the anhydrous state, as follows:

$$(0.9\pm 0.3)M_2O/n:Al_2O_3:zSiO_2$$

wherein M is a mixture of at least one of the quaternary cations of a Group V-A element of the Periodic Table and alkali metal cations, especially sodium and z is at least 10. The original cations can be present so that the amount of quaternary metal cations is between 10 and 90 percent of the total amount of the original cations. Thus, the zeolite can be expressed by the following formula in terms of mole ratios of oxides:

$$(0.9\pm 0.2)(xXR_4+(1-x)M_2O/n):Al_2O_3:zSiO_2$$

wherein R is an alkyl or aryl group having between 1 and 7 carbon atoms, M is an alkali metal cation, X is a Group V-A element, especially a metal, and x is between 0.1 and 0.9, and z is at least 10.

Zeolite ZSM-12 is taught by U.S. Pat. No. 3,832,449, issued Aug. 27, 1974, the disclosure of which is incorporated herein by reference. In the as synthesized form, the zeolite ZSM-12 for use in the catalyst composition useful in this invention has a formula, in terms of mole ratios of oxides in the anhydrous state, as follows:

$$(0.9\pm 0.3)M_2O/n:Al_2O_3:wSiO_2$$

wherein M is at least one cation having the valence n, w is at least 20, and has a characteristic X-ray diffraction pattern.

ZSM-35 is described by U.S. Pat. No. 4,016,245, the disclosure of which is incorporated herein by reference. This zeolite can be identified, in terms of mole ratios of oxides and in the anhydrous state, as follows:

$$(0.3\ to\ 2.5)R_2O:(0\ to\ 0.8)M_2O:Al_2O_3:xSiO_2$$

wherein R is an organic cation, M is an alkali metal cation and x is greater than 8, and is characterized by a specified X-ray powder diffraction pattern.

In a preferred synthesized form, zeolite ZSM-35 has a formula, in terms of mole ratios of oxides and in the anhydrous state, as follows:

$$(0.4\ to\ 2.5)R_2O:(0\ to\ 0.6)M_2O:Al_2O_3:ySiO_2$$

wherein R is an organic nitrogen-containing cation derived from ethylenediamine, pyrrolidine, butanediamine or an N-methylpyridinium compound, such as, for example, the hydroxide, halide, sulfate or nitrate, M is an alkali metal, especially sodium, and y is from greater than 8 to about 50.

ZSM-38 is described in U.S. Pat. No. 4,046,950, the disclosure of which is incorporated herein by reference. This zeolite can be identified, in terms of mole ratios or oxides and in the anhydrous state, as follows:

$$(0.3\ to\ 2.5)R_2O:(0\ to\ 0.8)M_2O:Al_2O_3:xSiO_2$$

wherein R is an organic cation, M is an alkali metal cation and x is greater than 8, and is characterized by a specified X-ray powder diffraction pattern.

In a preferred synthesized form, zeolite ZSM-38 has a formula, in terms of mole ratios of oxides and in the anhydrous state, as follows:

$$(0.4\ to\ 2.5)R_2O:(0\ to\ 0.6)M_2O:Al_2O_3:ySiO_2$$

wherein R is an organic nitrogen-containing cation derived from a 2-(hydroxyalkyl) trialkylammonium compound, wherein alkyl is methyl, ethyl or a combination thereof, M is an alkali metal, especially sodium, and y is from greater than 8 to about 50.

Another zeolite characterized as above and, therefore, useful as a catalyst component for the present process is described in U.S. application Ser. No. 878,558, filed Feb. 17, 1978. The zeolite, possessing a definite distinguishing crystalline structure whose X-ray diffraction pattern shows substantially the significant lines set forth in U.S. Pat. No. 3,702,886 for zeolite ZSM-5, can be identified, in terms of mole ratios of oxides in the anhydrous state, as follows:

$$(R_2O,M'_2O/n)_w:(Al_2O_3)_x:(SiO_2)_y:(M''_2O/n)_z$$

wherein W/X is from greater than 0.5 to less than 3, Y/X is greater than 20 and Z/X is from greater than zero to less than about 100, R is a nitrogen-containing cation and n is the valence of M' or M''. The function R may include primary amines containing 2 to 10 carbon atoms and ammonium cations, preferably the tetraalkylammonium cation in which the alkyl contains from 2 to 5 carbon atoms. The function M' is a metal from Group IA of the Periodic Table, ammonium, hydrogen or mixtures thereof. The function M'' is a metal, preferably selected from the group consisting of rare earth metals (i.e. metals having atomic numbers from 57 to 71), chromium, vanadium, molybdenum, indium, boron, mercury, tellurium, silver and one of the platinum group metals, which latter group includes platinum, palladium and ruthenium.

Although the zeolites herein described have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning to restore activity. In many environments the zeolites of this class exhibit long times on stream between burning regenerations.

An important characteristic of the crystal structure of the zeolites for use herein is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30.

The present invention provides a highly effective vapor phase isomeization process with a catalyst, the crystalline aluminosilicate zeolite portion of which, as suggested above, has a smaller pore size than those crystalline aluminosilicates previously used for such purpose.

The type zeolites useful in this invention freely sorb normal hexane and have a pore dimension greater than about 5 Angstroms. In addition, the structure must provide constrained access to large molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. Also, structures can be conceived due to pore blockage or other cause, that may be operative.

Rather than attempt to judge from crystal structure whether or not a catalyst possesses the necessary constrained access, a simple determination of the "contraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts, including those useful herein, are

| Crystalline Aluminosilicate | CI |
|---|---|
| ZSM-5 | 8.3 |
| ZSM-11 | 8.7 |
| Clinoptilolite | 3.4 |
| ZSM-12 | 2 |
| ZSM-35 | 2 |
| ZSM-38 | 2 |
| Beta | 0.6 |
| ZSM-4 | 0.5 |
| H-Zeolon | 0.5 |
| REY | 0.4 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The specific zeolites described, when prepared in the presence of organic cations, are catalytically inactive, possibly because the intracrystalline free space is occupied by organic cations from the forming solution. They may be activated by heating, for example, in an inert atmosphere at 1000° F. for one hour, followed by base exchange with ammonium salts and by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-35 and ZSM-38, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired for the present process. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and and stability of this class of zeolite is associated with its high crystal anionic framework density of not less than about 1.6 grams per cubic centimeter. This high density of course must be associated with a relatively small amount of free space within the crsytal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 | .38 | 1.65 |
| Heulandite | .39 | 1.69 |
| P | .41 | 1.57 |

-continued

| Zeolite | Void Volume | Framework Density |
|---|---|---|
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

Members of the above group of zeolites for use in the catalyst composition of the present invention possess definite distinguishing crystalline structures as evidenced by the above U.S. Patents incorporated herein by reference.

Zeolites ZSM-5, ZSM-11, ZSM-12, ZSM-35 and ZSM-38 for use in the process of this invention are prepared as indicated in the patents incorporated herein by reference above.

The zeolite described in U.S. application Ser. No. 878,558, filed Feb. 17, 1978 can be prepared utilizing materials which supply the appropriate components of the zeolite. Such components include sodium aluminate, alumina, sodium silicate, silica hydrosol, silica gel, silicic acid, sodium hydroxide and a tetrapropylammonium compound, e.g., tetrapropylammonium hydroxide. It will be understood that each component utilized in the reaction mixture for preparing the zeolite can be supplied by one or more initial reactants and they can be mixed together in any order. For example, sodium can be supplied by an aqueous solution of sodium hydroxide, or by an aqueous solution of sodium silicate; tetrapropylammonium cation can be supplied by the bromide salt. The reaction mixture can be prepared either batchwise or continuously. Crystal size and crystallization time of the composition will vary with the nature of the reaction mixture employed. It will be further understood that in the very high silica-to-alumina ratios, which can for this zeolite range from greater than 35 to about 3000 or more, and preferably from about 70 to about 500, it may not be necessary to add a source of alumina to the reaction mixture since residual amounts in other reactants may suffice.

The zeolite described in U.S. application Ser. No. 878,558 may be prepared from a reaction mixture having a composition, in terms of mole ratios of oxides or in moles of oxides, falling within the following ranges:

| | Broad | Preferred | Most Preferred |
|---|---|---|---|
| $OH^-/SiO_2$ | 0.07–1.0 | 0.1–0.8 | 0.2–0.75 |
| $R_4N^+/(R_4N^+ + Na^+)$ | 0.2–0.95 | 0.3–0.9 | 0.4–0.9 |
| $H_2O/OH^-$ | 10–300 | 10–300 | 10–300 |
| $SiO_2/Al_2O_3$ | 50–3000 | 70–1000 | 70–500 |
| Other metal oxides (% of total oxides) | $10^{-6}$–1.0 | $10^{-5}$–0.1 | $10^{-5}$–0.01 | wherein R is as above defined.

Typical reaction conditions for preparation of the zeolite described in U.S. application Ser. No. 878,558 consist of heating the foregoing reaction mixture to a temperature of from about 200° F. to 350° F. for a period of time of from about six hours to 120 days. A more preferred temperature range is from about 212° F. to 350° F. with the amount of time at a temperature in such range being from about 12 hours to 8 days. The digestion of the gel particles is carried out until crystals form.

The solid product is separated from the reaction medium, as by cooling the whole to room temperature, filtering and water washing. The foregoing product is dried, e.g. at 110° C. for from about 8 to 24 hours. Of course, milder conditions may be employed if desired, e.g. room temperature under vacuum.

For the improved isomerization process of this invention, the suitable zeolite catalyst is employed in combination with a support or binder material which acts as diluent such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of suitable crystalline aluminosilicate zeolite of the total composition of catalyst and binder or support may vary with the zeolite content ranging from between about 10 to about 90 percent by weight and more usually in the range of about 20 to about 80 percent by weight of the composition.

Operating conditions employed in the improved process of the present invention are important. Such conditions as temperature, pressure, space velocity, molar ratio of the reactants, hydrogen to hydrocarbon mole ratio, and the presence of any feedstock diluents, such as toluene and/or $C_9^+$ recycle material, will have important effects on the process.

The process of this invention is conducted such that isomerization of the monocyclic methyl-substituted aromatic hydrocarbon of from 8 to 10 carbon atoms contained in a feedstock which also contains ethylbenzene is carried out in the vapor phase by contact in a reaction zone, such as, for example, a fixed bed, with the above-described catalyst under isomerization effective conditions, said catalyst being characterized, as synthesized, as containing the above-defined zeolite which may or may not have been hydrogen or hydrogen precursor exchanged and Group VIII metal exchanged. This process may be conducted in either fixed or fluid bed operation with attendant benefits of either operation readily obtainable.

The present improved isomerization process must be carried out at a temperature between about 600° F. and about 900° F. and at pressures ranging from about 0 psig to about 500 psig. The weight hourly space velocities (WHSV) based on weight of total catalyst may be maintained at from about 0.1 hr$^{-1}$ to about 200 hr$^{-1}$, and a hydrogen/hydrocarbon mole ratio of from 0 to about 10. Within these limits the conditions of temperature and pressure will vary considerably depending upon equilibrium considerations and type of feed material. Optimum conditions are those in which maximum yields of desired isomer products are obtained and hence considerations of temperature and pressure will vary within a range of conversion levels designed to provide the highest selectivity and maximum yield.

The feedstock to be employed in the present improved process contains single ring aromatic hydrocarbons containing a minimum of two and a maximum of four methyl group substituents on the ring. These feed materials may be illustrated by the following structural formula:

wherein R is methyl and n is an integer of 2 to 4. The amount of ethylbenzene to be found in the feedstock will vary from about 5 to about 30 weight percent, and more usually from about 10 to about 25 weight percent.

Specific compounds falling within the above structural formula include para-xylene, meta-xylene, ortho-xylene, mesitylene (1,3,5-trimethylbenzene), durene (1,2,4,5-tetramethylbenzene), hemimellitene (1,2,3-trimethylbenzene), pseudocumene (1,2,4-trimethylbenzene), prehnitene (1,2,3,4-tetramethylbenzene) and isodurene (1,2,3,5-tetramethylbenzene).

Of the above listing of specific feed materials which may be isomerized, the xylene isomers and pseudocumene are especially preferred.

The nitrogen-containing compounds useful in the present process should be ones which neither react with the charge materials nor possess catalytic activity contrary to the purpose for their use. Said nitrogen-containing compounds may be gaseous, liquid or in the form of a solid dissolved in a suitable solvent, such as, for example, toluene.

Non-limiting examples of nitrogen compounds or precursors thereof useful in this invention include, for example, ammonia, alkylamines of from 1 to about 40 carbon atoms, and preferably from 1 to about 10 carbon atoms, e.g. n-propylamine, alkyldiamines of from 2 to about 40 carbon atoms, and preferably from 6 to about 20 carbon atoms, aromatic amines of from 6 to about 40 carbon atoms, e.g. aniline, and heterocyclic nitrogen compounds, such as pyridine and pyrrolidine.

The catalyst may be contacted with the nitrogen compound in a variety of ways. For example, the nitrogen compound can be contacted with the catalyst during manufacture of the catalyst, prior to introducing the normal feedstock, or it can be added to the feedstock periodically or continuously. Combinations of these modes of addition are also contemplated.

The specific examples, hereinafter discussed, will serve to illustrate the process of the present invention without unduly limiting same.

EXAMPLE 1

A sodium silicate solution was prepared by mixing 16 parts water and 27.7 parts sodium silicate (28.7 wt.% $SiO_2$, 8.9 wt.% $Na_2O$, 62.4% $H_2O$). The solution was cooled to approximately 15° C.

An acid solution was prepared by adding 1 part aluminum sulfate (17.2 wt.% $Al_2O_3$) to 16.4 parts water followed by 2.4 parts sulfuric acid (93 wt.% $H_2SO_4$) and 1.2 parts NaCl.

These solutions were mixed in an agitated vessel while 3.9 parts of NaCl were added. The gel molar ratios expressed as oxides are the following:
$SiO_2/Al_2O_3=78.4$
$Na_2O/Al_2O_3=49.9$ An organic solution was prepared by adding 1.6 parts n-propyl bromide and 3.1 parts methyl ethyl ketone to 1.9 parts tri-n-propylamine.

After the gel was heated to about 95° C., agitation was reduced and the organic solution was added above the gel. This mixture was held at about 95°–110° C. for 14 hours, then agitation was increased. When approximately 65% of gel was crystallized the temperature was increased to about 150°–160° C. and held there until crystallization was complete. Unreacted organics were removed by flashing and the remaining contents cooled.

The zeolite slurry product was diluted with 4–5 parts water per part slurry, allowed to settle and supernatant liquid was drawn off. The settled solids were reslurried to the original volume of the preceding step with water. After settling, the aqueous phase was decanted. This procedure was repeated until the sodium level of the zeolite was less than 1.0 wt.%. The washed zeolite was then filtered, dried and identified as ZSM-5 having a silica/alumina mole ratio of at least 12; i.e., about 70, and a constraint index of between 1 and 12; i.e., about 8.3.

The dried zeolite was then mixed with alumina and water. It was then extruded into 1/16" pellets and dried. The extruded material contained 65 parts ZSM-5 per 35 parts alumina.

The dried extrudate was calcined for three hours at 538° C. in flowing nitrogen. After cooling, the extrudate was contacted with an ammonium nitrate exchange solution (about 0.08 lb NH$_4$NO$_3$/lb extrudate) for one hour at ambient temperature. This exchange was then repeated until the sodium level was less than 0.05 wt.%. The extrudate was then contacted with a nickel nitrate exchange solution (about 0.1 lb Ni(Ni(NO$_3$)$_2$.6H$_2$O/lb extrudate) for two hours at about 80°–90° C. After this exchange, the extrudate was washed, dried and calcined in a flowing 10% air—90% nitrogen gas mixture at 538° C. for six hours.

EXAMPLE 2

A 25 cc quantity of the catalyst material of Example 1 was further calcined at 1000° F. in air for 24 hours and placed in an isothermal, one gallon/day reactor. Pure hydrogen gas was continuously passed through the reactor without recycle in order to maintain a constant molar ratio between hydrogen and hydrocarbon feedstock at the reactor inlet. A feedstock comprised of the components listed in Table 2, hereinafter presented, was then passed through the reactor under the conditions listed in Table 3, hereinafter presented. Also listed in Table 3 are the results of ten separate material balances over the period of 10.5 days on stream. It will be noted that from the data generated at each material balance, an approach to equilibrium was calculated as being (weight % p- or o-isomer, respectively, of total xylenes produced - weight % of that isomer in the feed) divided by (equilibrium weight % concentration of p- or o-isomer, respectively at the reaction temperature - weight % of that isomer in feed). The p- or o-isomer equilibrium concentrations, respectively, as a function of reaction temperature may be determined according to *The Chemical Thermodynamics of Organic Compounds* by Stull, Westrum and Sinke, published in 1969 by Wiley.

TABLE 2

| Feedstock Composition for Example 2 | |
|---|---|
| Component | Amount, wt. % |
| Toluene | 0.04 |
| Ethylbenzene | 14.81 |
| p-Xylene | 10.07 |
| m-Xylene | 59.29 |
| O-Xylene | 15.69 |
| C$_9$+ Aromatics | 0.11 |

TABLE 3

| EXAMPLE 2 REACTION CONDITIONS AND RESULTS | | | | | | | | | | |
|---|---|---|---|---|---|---|---|---|---|---|
| Material Balance | 1 | 2 | 3 | 4 | 5 | 6 | 7 | 8 | 9 | 10 |
| Days on Stream | 0.8 | 1.9 | 2.9 | 4.8 | 5.5 | 6.5 | 7.5 | 8.5 | 9.5 | 10.5 |
| Temperature, °F. | 541 | 542 | 561 | 560 | 581 | 581 | 601 | 601 | 621 | 620 |
| WHSV, hr.$^{-1}$ | 7.14 | 7.21 | 7.25 | 7.20 | 7.26 | 7.17 | 7.25 | 7.25 | 7.20 | 7.19 |
| Pressure, psig | 200 | 200 | 200 | 200 | 200 | 200 | 200 | 200 | 200 | 200 |
| H2/HC Ratio | 4.07 | 4.00 | 3.98 | 4.05 | 4.02 | 4.03 | 3.99 | 3.99 | 3.78 | 3.96 |
| Ethylbenzene Conversion, mole % | 3.63 | 3.69 | 6.58 | 6.64 | 11.19 | 11.77 | 17.95 | 18.40 | 26.53 | 26.77 |
| Xylene Loss, mole % | .46 | .49 | .92 | 1.11 | 1.69 | 1.73 | 2.77 | 2.63 | 3.92 | 3.95 |
| Approach to Equilibrium for p-xylene | 100.5 | 100.5 | 101.4 | 101.1 | 100.6 | 101.5 | | | | |
| Approach to Equilibrium for o-xylene | 60.8 | 65.4 | 73.1 | 72.1 | 77.7 | 77.1 | 79.9 | 79.8 | 81.1 | 79.8 |
| Yields, mole % | | | | | | | | | | |
| Benzene | .43 | .43 | .75 | .77 | 1.32 | 1.32 | 2.22 | 2.16 | 3.35 | 3.31 |
| Toluene | .30 | .33 | .45 | .50 | .68 | .68 | .88 | .86 | 1.16 | 1.16 |
| Ethylbenzene | 14.27 | 14.26 | 13.84 | 13.83 | 13.15 | 13.07 | 12.15 | 12.09 | 10.88 | 10.85 |
| p-Xylene | 20.08 | 20.07 | 20.19 | 20.21 | 20.05 | 20.05 | 19.88 | 19.88 | 19.52 | 19.60 |
| m-Xylene | 47.24 | 47.10 | 46.32 | 46.21 | 45.65 | 45.64 | 44.87 | 44.97 | 44.28 | 44.23 |
| o-Xylene | 17.33 | 17.46 | 17.75 | 17.68 | 17.91 | 17.88 | 17.94 | 17.96 | 17.91 | 17.85 |
| Methylethylbenzene | .06 | .08 | .10 | .13 | .17 | .18 | .22 | .22 | .28 | .29 |
| Trimethylbenzene | .09 | .08 | .17 | .18 | .23 | .26 | .35 | .35 | .45 | .47 |
| Diethylbenzene | .11 | .11 | .22 | .24 | .40 | .42 | .63 | .65 | .83 | .86 |
| Dimethylethylbenzene | .08 | .09 | .21 | .25 | .45 | .51 | .84 | .87 | 1.33 | 1.39 |

EXAMPLE 3

After 10.5 days on stream, the catalyst material used in Example 2 was contacted in the same reactor as for Example 2 with a feedstock containing a nitrogen-containing compound, i.e., 1,10-decane diamine as indicated in Table 4, hereinafter presented. The feedstock containing the nitrogen-containing compound was pumped through the reactor for 24 hours at operating conditions of 600° F., 200 psig, a WHSV of 7 hr$^{-1}$ and a hydrogen/hydrocarbon mole ratio of 4. The ratio of nitrogen atoms provided in the feed per aluminum atom in the zeolite component was 3.4.

Thereafter, the above feedstock without the nitrogen-containing compound was charged to the reactor and at the reaction conditions of Example 2, the catalyst was found to be inactive. The reaction temperature was increased, through increments, up to about 750° F., where a rapid reactivation of the catalyst was observed as a result of desorption of part of the nitrogen from the catalyst, bringing the ratio of nitrogen atoms/aluminum atom in the zeolite component within the range of 0.01 to 1.0. The temperature was then reduced to 700° F. where gradual recovery of catalyst activity was still observable. The reaction conditions and results from 8 material balances over the period of about 8 days on stream appear in Table 5.

EXAMPLE 4

The experiment of Example 3 was continued with a feedstock composed as indicated in Table 6, hereinafter presented. The conditions for and results from 10 material balances over a period of about 10 days on stream appear in Table 7.

TABLE 4

| Feedstock Composition for Example 3 Containing a Nitrogen-Containing Compound | |
|---|---|
| Component | Amount |
| 1,10-Decane diamine | ~ 500 pm |
| Toluene | 0.04 wt % |
| Ethylbenzene | 15.60 wt % |
| p-Xylene | 11.53 wt % |
| m-Xylene | 57.72 wt % |
| o-Xylene | 15.02 wt % |
| $C_9^+$ Aromatics | 0.09 wt T |

TABLE 6

| Feedstock Composition for Example 4 | |
|---|---|
| Component | Amount, wt. % |
| Toluene | 0.04 |
| Ethylbenzene | 15.20 |
| p-Xylene | 10.26 |
| m-Xylene | 59.86 |
| o-Xylene | 14.55 |
| $C_9^+$ Aromatics | 0.08 |

TABLE 5

| EXAMPLE 3 REACTION CONDITIONS AND RESULTS | | | | | | | | |
|---|---|---|---|---|---|---|---|---|
| Material Balance | 11 | 12 | 13 | 14 | 15 | 16 | 17 | 18 |
| Days on Stream | 24.3 | 25.2 | 26.2 | 27.1 | 28.2 | 29.8 | 31.1 | 32.1 |
| Temperature, °F. | 600 | 600 | 650 | 700 | 752 | 751 | 750 | 700 |
| WHSV, hr.$^{-1}$ | 7.19 | 7.14 | 7.18 | 7.18 | 7.24 | 7.22 | 7.12 | 7.31 |
| Pressure, psig | 200 | 200 | 200 | 200 | 200 | 200 | 200 | 200 |
| H2/HC Ratio | 4.01 | 4.04 | 4.00 | 3.98 | 3.95 | 4.00 | 4.03 | 3.95 |
| Ethylbenzene Conversion, mole % | .00 | −.18 | 1.02 | 1.18 | 19.95 | 33.71 | 36.57 | 20.35 |
| Xylene Loss, mole % | .11 | .07 | −.21 | −.16 | 1.58 | 2.91 | 3.68 | 1.89 |
| Activity Loss, °F. | 179 | | 159 | 205 | 149 | 122 | 117 | 94 |
| Approach to Equilibrium for p-Xylene | .6 | .5 | 2.6 | 30.6 | 101.3 | 101.8 | 102.4 | 100.9 |
| Approach to Equilibrium for o-Xylene | .8 | −.2 | −3.9 | 21.6 | 80.1 | 80.1 | 82.7 | 82.3 |
| Yields, mole % | | | | | | | | |
| Benzene | .00 | .00 | .00 | .10 | 2.84 | 4.74 | 5.30 | 2.78 |
| Toluene | .12 | .06 | .03 | .04 | .28 | .55 | .71 | .33 |
| Ethylbenzene | 15.60 | 15.63 | 15.44 | 15.42 | 12.49 | 10.34 | 9.89 | 12.43 |
| Paraxylene | 11.57 | 11.57 | 11.78 | 14.12 | 19.62 | 19.39 | 19.29 | 19.61 |
| Metaxylene | 57.58 | 57.64 | 57.79 | 54.19 | 44.42 | 43.78 | 43.26 | 44.43 |
| Orthoxylene | 15.04 | 15.00 | 14.88 | 16.09 | 18.90 | 18.64 | 18.62 | 18.63 |
| Propylbenzene | .08 | .08 | .07 | .04 | .00 | .00 | .00 | .00 |
| Methylethylbenzene | .00 | .00 | .00 | .00 | .05 | .12 | .17 | .07 |
| Trimethylbenzene | .02 | .02 | .01 | .00 | .08 | .17 | .21 | .08 |
| Diethylbenzene | .00 | .00 | .00 | .01 | .65 | .97 | 1.02 | .80 |
| Dimethylethylbenzene | .00 | .00 | .00 | .00 | .67 | 1.29 | 1.53 | .84 |

TABLE 7

| EXAMPLE 4 REACTION CONDITIONS AND RESULTS | | | | | | | | | | |
|---|---|---|---|---|---|---|---|---|---|---|
| Material Balance | 19 | 20 | 21 | 22 | 23 | 24 | 25 | 26 | 27 | 28 |
| Days on Stream | 34.1 | 36.1 | 37.1 | 38.1 | 39.1 | 40.1 | 41.1 | 42.1 | 43.1 | 44.8 |
| Temperature, °F. | 700 | 701 | 701 | 701 | 700 | 700 | 700 | 700 | 700 | 700 |
| WHSV, hr.$^{-1}$ | 7.19 | 7.22 | 7.22 | 7.21 | 7.22 | 7.22 | 7.25 | 7.14 | 7.12 | 7.19 |
| Pressure, psig | 200 | 200 | 200 | 200 | 200 | 200 | 200 | 200 | 200 | 200 |
| H2/HC Ratio | 3.97 | 3.86 | 3.92 | 3.93 | 3.93 | 3.93 | 3.91 | 3.98 | 3.97 | 3.94 |
| Ethylbenzene Conversion, mole % | 20.41 | 21.75 | 22.42 | 23.04 | 23.32 | 23.49 | 23.93 | 24.12 | 24.88 | 25.34 |
| Xylene Loss, mole % | 1.86 | 1.84 | 1.99 | 1.92 | 2.00 | 1.88 | 2.03 | 2.13 | 2.01 | 2.15 |
| Activity Loss, °F. | 96 | 94 | 92 | 91 | 90 | 89 | 89 | 88 | 87 | 86 |
| Approach to Equilibrium for p-Xylene | 101.1 | 100.8 | 101.2 | 100.7 | 100.9 | 100.3 | 100.9 | 101.6 | 100.5 | 100.9 |
| Approach to Equilibrium for o-Xylene | 81.4 | 81.5 | 81.1 | 80.1 | 76.5 | 84.9 | 82.7 | 82.8 | 79.1 | 78.6 |
| Yields, mole % | | | | | | | | | | |
| Benzene | 2.67 | 2.84 | 2.96 | 3.03 | 3.00 | 3.04 | 3.17 | 3.10 | 3.19 | 3.43 |
| Toluene | .33 | .35 | .36 | .36 | .36 | .37 | .38 | .41 | .40 | .42 |
| Ethylbenzene | 12.10 | 11.90 | 11.79 | 11.70 | 11.66 | 11.63 | 11.57 | 11.54 | 11.42 | 11.35 |
| Paraxylene | 19.75 | 19.72 | 19.72 | 19.69 | 19.70 | 19.66 | 19.69 | 19.74 | 19.66 | 19.67 |
| Metaxylene | 44.77 | 44.79 | 44.72 | 44.84 | 44.98 | 44.65 | 44.64 | 44.52 | 44.88 | 44.80 |
| Orthoxylene | 18.59 | 18.60 | 18.55 | 18.51 | 18.30 | 18.77 | 18.62 | 18.61 | 18.43 | 18.38 |
| Methylethylbenzene | .07 | .07 | .07 | .07 | .07 | .07 | .08 | .08 | .08 | .08 |
| Trimethylbenzene | .09 | .09 | .10 | .09 | .16 | .10 | .10 | .11 | .10 | .11 |
| Diethylbenzene | .77 | .78 | .83 | .81 | .84 | .83 | .83 | .90 | .85 | .85 |
| Dimethylethylbenzene | .86 | .85 | .89 | .90 | .93 | .88 | .92 | .99 | .99 | .92 |

Figure 1:
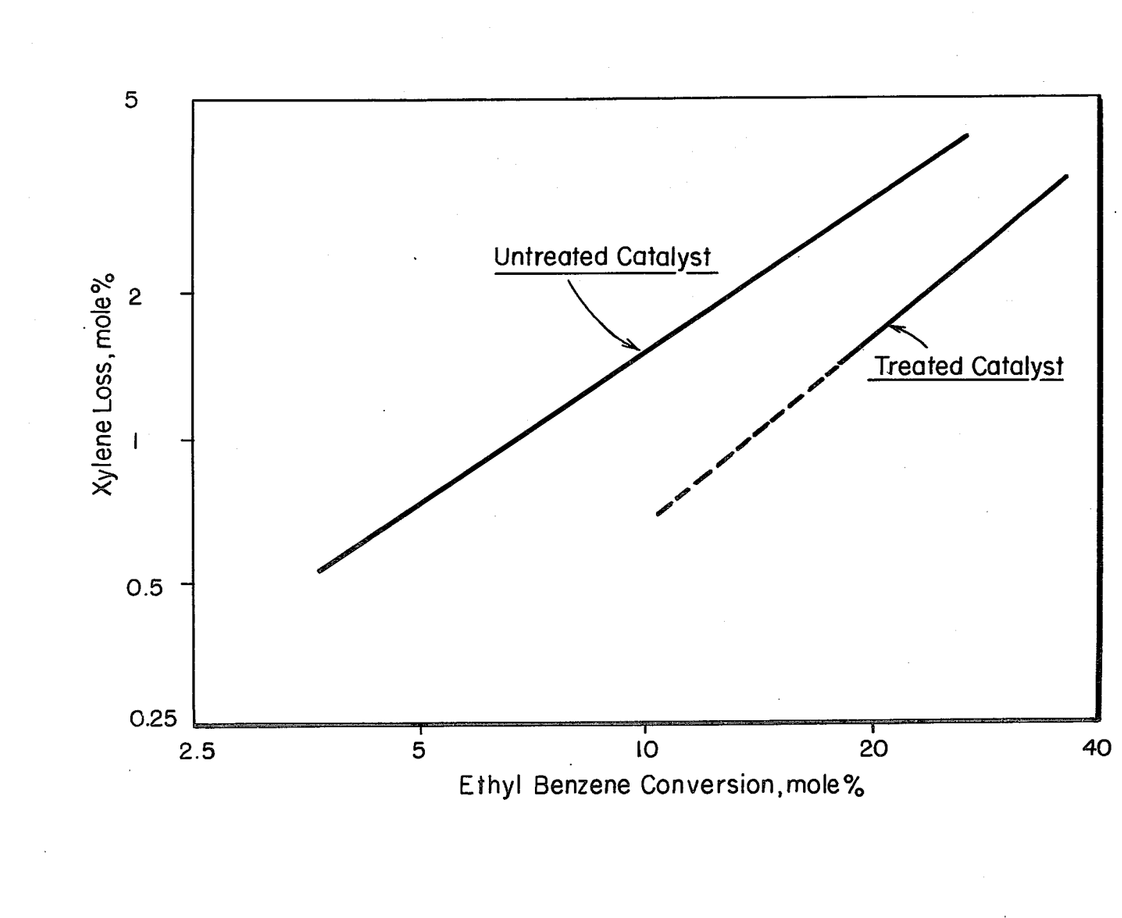

A plot of ethylbenzene conversion v. xylene loss for the results of Example 2, Example 3 and Example 4 is presented in the figure attached hereto. It is readily observed that at a particular ethylbenzene conversion, the process of the present invention, whereby the catalyst has been treated with a nitrogen-containing compound, exhibits substantially reduced xylene loss. This reduction in xylene loss for isomerization of xylenes is an unexpected and significant benefit and indicates that, whatever the monocyclic methyl-substituted aromatic hydrocarbon feedstock may be, substantial reduction in primary product losses will be effected and selectivity to desired product isomer will be enhanced.

EXAMPLE 5

A quantity of catalyst prepared as in Example 1 except without contact with the nickel nitrate exchange solution was placed in a reactor as used in Examples 2–4. A feedstock composed as described in Table 8, hereinafter presented was then passed through the reactor at 25 psig, 600° F., a WHSV of 5 hr$^{-1}$ and a hydrogen/hydrocarbon mole ratio of 0 (absence of added hydrogen). The results of this experiment are presented in Table 9, hereinafter presented.

EXAMPLE 6

The feedstock for Example 5 is then injected with ammonia to the extent that the ratio of nitrogen atoms/aluminum atom in the zeolite is 0.1. The injection of ammonia into the feedstock is stopped after a time and the reaction temperature is increased to 750° F. Results of this experiment are also presented in Table 9 for comparison with the results from Example 5.

TABLE 8

| Feedstock Composition for Example 5 | |
|---|---|
| Component | Amount, wt. % |
| Toluene | 0.9 |
| Ethylbenzene | 6.9 |
| p-Xylene | 10.5 |
| m-Xylene | 62.9 |
| o-Xylene | 18.7 |
| $C_9^+$ Aromatics | — |

TABLE 9

| Results from Examples 5 and 6 | | |
|---|---|---|
| Example | 5 | 6 |
| Ethylbenzene Conversion, Wt. % | 24.6 | 24.6 |
| Xylene Loss, wt. % | 1.84 | 0.87 |
| Approach to Equilibrium for p-Xylene | 102.8 | 102.0 |
| Yield, Wt. % | | |
| $C_1$–$C_5$ hydrocarbons | — | 0.1 |
| Benzene | 0.7 | 1.2 |
| Toluene | 1.7 | 1.1 |
| Ethylbenzene | 5.2 | 5.2 |
| p-Xylene | 21.9 | 21.7 |
| m-Xylene | 49.0 | 48.6 |
| o-Xylene | 19.5 | 21.0 |
| $C_9^+$ Aromatics | 2.0 | 1.1 |

What is claimed is:

1. A process for effecting catalytic isomerization of monocyclic methyl-substituted aromatic hydrocarbon compounds of from 8 to 10 carbon atoms contained in a feedstock also containing ethylbenzene which comprises contacting said feedstock in the vapor phase with a catalyst containing crystalline aluminosilicate zeolite characterized by a constant index within the approximate range of 1 to 12, said zeolite containing cations which are selected from the group consisting of hydrogen, hydrogen precursor and metal of Group VIII of the Periodic Table of Elements, at a temperature of from about 600° F. to about 900° F., a pressure of from about 0 psig to about 500 psig, a hydrogen/hydrocarbon mole ratio of from 0 to about 10 and a weight hourly space velocity of from about 0.1 hr$^{-1}$ to about 200 hr$^{-1}$, said catalyst being contacted with one or more basic nitrogen compounds or precursors thereof such that the ratio of nitrogen atoms/aluminum atom in the zeolite is from about 0.01 to about 1.0.

2. The process of claim 1 wherein said zeolite is ZSM-5, ZSM-11, ZSM-12, ZSM-35 or ZSM-38.

3. The process of claim 2 wherein said zeolite is ZSM-5.

4. The process of claim 1 wherein said zeolite is combined in an amount of from about 10 to about 90 weight percent in a binder thereof.

5. The process of claim 4 wherein said binder is alumina.

6. The process of claim 2 wherein said zeolite is combined in an amount of from about 10 to about 90 weight percent in a binder therefor.

7. The process of claim 6 wherein said binder is alumina.

8. The process of claim 3 wherein said zeolite is combined in an amount of from about 10 to about 90 weight percent in a binder therefor.

9. The process of claim 8 wherein said binder is alumina.

10. The process of claim 1 wherein said Group VIII metal cations are selected from the group consisting of nickel, iron, cobalt and mixtures thereof.

11. The process of claim 10 wherein said Group VIII metal cations are nickel.

12. The process of claim 2 wherein said Group VIII metal cations are selected from the group consisting of nickel, iron, cobalt and mixtures thereof.

13. The process of claim 12 wherein said Group VIII metal cations are nickel.

14. The process of claim 3 wherein said group VIII metal cations are selected from the group consisting of nickel, iron, cobalt and mixtures thereof.

15. The process of claim 14 wherein said group VIII metal cations are nickel.

16. The process of claim 1 wherein said feedstock contains materials illustrated by the formula:

wherein R is methyl and n is an integer of from 2 to 4.

17. The process of claim 2 wherein said feedstock contains materials illustrated by the formula:

wherein R is methyl and n is an integer of from 2 to 4.

18. The process of claim 3 wherein said feedstock contains materials illustrated by the formula:

wherein R is methyl and n is an integer of from 2 to 4.

19. The process of claim 10 wherein said feedstock contains materials illustrated by the formula:

wherein R is methyl and n is an integer of from 2 to 4.

20. The process of claim 12 wherein said feedstock contains materials illustrated by the formula:

wherein R is methyl and n is an integer of from 2 to 4.

21. The process of claim 14 wherein said feedstock contains materials illustrated by the formula:

wherein R is methyl and n is an integer of from 2 to 4.

22. The process of claim 16 wherein said feedstock contains xylenes.

23. The process of claim 17 wherein said feedstock contains xylenes.

24. The process of claim 18 wherein said feedstock contains xylenes.

25. The process of claim 1 wherein said basic nitrogen compounds or precursors thereof are selected from the group consisting of ammonia, alkylamines of from 1 to about 40 carbon atoms, alkyldiamines of from 2 to about 40 carbon atoms, aromatic amines of from 6 to about 40 carbon atoms, pyridine, pyrrolidine and aniline.

26. The process of claim 2 wherein said basic nitrogen compounds or precursors thereof are selected from the group consisting of ammonia, alkylamines of from 1 to about 40 carbon atoms, alkyldiamines of from 2 to about 40 carbon atoms, aromatic amines of from 6 to about 40 carbon atoms, pyridine, pyrrolidine and aniline.

27. The process of claim 3 wherein said basic nitrogen compounds or precursors thereof are selected from the group consisting of ammonia, alkylamines of from 1 to about 40 carbon atoms, alkyldiamines of from 2 to about 40 carbon atoms, aromatic amines of from 6 to about 40 carbon atoms, pyridine, pyrrolidine and aniline.

28. The process of claim 10 wherein said basic nitrogen compounds or precursors thereof are selected from the group consisting of ammonia, alkylamines of from 1 to about 40 carbon atoms, alkyldiamines of from 2 to about 40 carbon atoms, aromatic amines of from 6 to about 40 carbon atoms, pyridine, pyrrolidine and aniline.

29. The process of claim 12 wherein said basic nitrogen compounds or precursors thereof are selected from the group consisting of ammonia, alkylamines of from 1 to about 40 carbon atoms, alkyldiamines of from 2 to about 40 carbon atoms, aromatic amines of from 6 to about 40 carbon atoms, pyridine, pyrrolidine and aniline.

30. The process of claim 14 wherein said basic nitrogen compounds or precursors thereof are selected from the group consisting of ammonia, alkylamines of from 1 to about 40 carbon atoms, alkyldiamines of from 2 to about 40 carbon atoms, aromatic amines of from 6 to about 40 carbon atoms, pyridine, pyrrolidine and aniline.

31. The process of claim 1 wherein said zeolite has the composition, in terms of mole ratios of oxides in the anhydrous state, as follows:

$$(R_2O, M'_{2/n}O)_w:(Al_2O_3)_x:(SiO_2)_y:(M''_2O)_z$$

wherein W/X is from greater than 0.5 to less than 3, Y/X is greater than 20 and Z/X is from greater than zero to less than about 100, R is a nitrogen-containing cation and n is the valence of M' and M''.

32. A process for effecting catalytic isomerization of monocyclic methyl-substituted aromatic hydrocarbon feedstock which comprises contacting said feedstock in the vapor phase with a catalyst containing crystalline aluminosilicate zeolite characterized by a silica/alumina mole ratio of greater than 12 and a constraint index within the approximate rate of 1 to 12, said zeolite containg cations which are selected from the group consisting of hydrogen, hydrogen precursor and metal of Group VIII of the Periodic Table of Elements, at a temperature of from about 600° F. to about 900° F., a pressure of from about 0 psig to about 500 psig, a hydrogen/hydrocarbon mole ratio of from 0 to about 10 and a weight hourly space velocity of from about 0.1 hr$^{-1}$ to about 200 hr$^{-1}$, said hydrogen/hydrocarbon mole ratio being 0 when said cations are hydrogen or hydrogen precursor and from 0.1 to about 10 when said cations include a metal of Group VIII of the Periodic Table of Elements, said catalyst being contacted with a basic nitrogen compound or precursor thereof such that the ratio of nitrogen atoms/aluminum atom in the zeolite is from about 0.01 to about 1.0.

* * * * *

UNITED STATES PATENT AND TRADEMARK OFFICE
CERTIFICATE OF CORRECTION

PATENT NO. : 4,158,676
DATED : June 19, 1979
INVENTOR(S) : F. A. Smith, L. L. Breckenridge and A. B. Schwartz It is certified that error appears in the above-identified patent and that said Letters Patent are hereby corrected as shown below:

Column 3, lines 17, 26, 37, 48 and 61, — In each formula "$M_2O/n$" should be
-- $M_{2/n}O$ --

Column 4, line 52 — In formula $M'_2O/n$" and $M''_2O/n$ should be
-- $M'_{2/n}O$ -- and $M''_{2/n}O$ --

TABLE 3, line reading "Approach to Equilibrium for p-Xylene " — should read across as:
-- 97.4  97.4  99.8  100.4  100.5  100.5  101.4  101.1  100.6  101.5 --

TABLE 3, last line — Dimethylethylbenzene (ACROSS) should read :
-- .08  .09  .21  .24  .45  .51  .83  .87  1.33  1.39 --

Column 16, line 18, Claim 4 — percent in a binder "thereof." should be
percent in a binder -- therefor. --

Column 18, line 28, Claim 38 — formula should read:

-- $(R_2O, M'_{\underline{2}\over n}O)_W : (Al_2O_3)_X : (SiO_2)_Y : (M''_{\underline{2}\over n}O)_Z$ --

UNITED STATES PATENT AND TRADEMARK OFFICE
CERTIFICATE OF CORRECTION

PATENT NO. : 4,158,676
DATED : June 19, 1979
INVENTOR(S) : F. A. Smith, L. L. Breckenridge and A. B. Schwartz It is certified that error appears in the above–identified patent and that said Letters Patent are hereby corrected as shown below:

Column 18, line 51, Claim 32 — "from 0.1 to about 10" should be -- from about 0.1 to about 10 --

Signed and Sealed this

Fifteenth Day of January 1980

[SEAL]

Attest:

SIDNEY A. DIAMOND

Attesting Officer

Commissioner of Patents and Trademarks